(12) United States Patent
Anderson

(10) Patent No.: US 6,199,985 B1
(45) Date of Patent: Mar. 13, 2001

(54) PUPILOMETER METHODS AND APPARATUS

(76) Inventor: Christopher Scott Anderson, 4556 Knollwood La., Niceville, FL (US) 32578

(*) Notice: Subject to any disclaimer, the term of this patent is extended or adjusted under 35 U.S.C. 154(b) by 0 days.

(21) Appl. No.: 09/312,094

(22) Filed: May 15, 1999

Related U.S. Application Data

(60) Provisional application No. 60/085,543, filed on May 15, 1998.

(51) Int. Cl.[7] .................................................. A61B 3/10
(52) U.S. Cl. ............................................................ 351/221
(58) Field of Search .................................... 351/200, 204, 351/205, 206, 208, 202, 209, 221; 600/558

(56) References Cited

U.S. PATENT DOCUMENTS

| | | |
|---|---|---|
| 3,450,468 | 6/1969 | Streisinger . |
| 3,473,868 | 10/1969 | Young et al. . |
| 3,689,135 | 9/1972 | Young et al. . |
| 4,012,128 | 3/1977 | Regan . |
| 4,102,563 | 7/1978 | Matsumura et al. . |
| 4,397,531 | 8/1983 | Lees . |
| 4,641,349 | 2/1987 | Flom et al. . |
| 4,712,895 | 12/1987 | Kamiyama et al. . |
| 4,755,043 | 7/1988 | Carter . |
| 4,850,691 | 7/1989 | Gardner et al. . |
| 4,967,186 | 10/1990 | Ludmirsky et al. . |
| 5,042,937 | 8/1991 | Cornsweet . |
| 5,114,222 | 5/1992 | Cornsweet . |
| 5,187,506 | 2/1993 | Carter . |
| 5,196,872 | 3/1993 | Beesmer et al. . |
| 5,210,554 | 5/1993 | Cornsweet et al. . |
| 5,410,376 | 4/1995 | Cornsweet et al. . |
| 5,646,709 | 7/1997 | Carter . |
| 5,661,538 | 8/1997 | Carter . |
| 5,704,369 | 1/1998 | Scinto et al. . |
| 5,790,235 | * 8/1998 | Kirschbaum ..................... 351/246 |
| 6,007,202 | * 12/1999 | Apple et al. ....................... 351/209 |

* cited by examiner

Primary Examiner—George Manuel
(74) Attorney, Agent, or Firm—Keith Frantz

(57) ABSTRACT

Apparatus for detecting and measuring pupillary size and response to a light stimulus includes a an IR source and optical apparatus for directing an IR beam toward an individuals pupil, a measuring channel comprising optical and photo-optical detecting apparatus for directing and receiving a first portion of the IR illumination leaving the individual's pupil and for providing an electrical output signal indicative of the illumination power detected, and a calibration channel comprising second optical and photo-optical apparatus adapted to receive a second portion of the IR illumination leaving the individual's pupil and for providing an electrical output signal indicative of certain individual-specific pupillary parameters. The output signal from the measuring channel, providing information regarding relative pupillary size changes when the pupil is light-stimulated, is processed with the output signal from the calibration channel to provide absolute or actual pupillary size and response data.

36 Claims, 2 Drawing Sheets

PUPILOMETER METHODS AND APPARATUS

CROSS-REFERENCES TO RELATED APPLICATION

This application claims the benefit of U.S. Provisional application No. 60/085,543, filed May 15, 1998.

BACKGROUND OF THE INVENTION

1. Field of Invention

This invention relates generally to methods and apparatus suitable for use in measuring and detecting certain pupillary size and response parameters. More particularly, the invention relates to such methods and apparatus which, while suitable for use in pupilometers and other opthamological instruments in general, is particularly suitable for use in portable and hand-held pupilometers.

2. Description of Prior Art

It is known that the response of an individual's pupil to external light stimulation yields useful information as to the subjects well being. Pupillometry is an effective and non-invasive means of characterizing a subject's pupillary response and is used to determine the condition of the subject's nervous system.

Pupillometry has been the subject of focus for applications such as diagnosing Alzeheimer's disease (see e.g., Scinto et al., U.S. Pat. No. 5,704,369, Non-Invasive Method for Diagnosing Alzeheimer's Disease in a Patient; and Carter, U.S. Pat. No. 5,646,709 Portable Hand-Held Pupillometer with Dynamic Electronic Image Centering Aid and Method of use Thereof), detecting fatigue as indicated by an individual's alertness or sleepiness, and detecting the presence of alcohol and chemical/substance abuse (see e.g., Carter, U.S. Pat. No. 5,187,506, Method and Apparatus for Determining Physiological Parameters Based on Pupil Response), for detecting other conditions related to nervous system impairment, and for other ophthamological diagnostic applications(see e.g., Cornsweet, U.S. Pat. No. 5,042,937, Optical System for an Opthamological Instrument for Examination of Pupillary Responses; and Zanecchia et al., U.S. Pat. No. 5,534,952, Pupillometer). Thus, pupilometers, and the method associated therewith, may be useful in the medical, transportation, and military and law enforcement fields, in industry, and in other areas in which it is desirable to detect such conditions.

For these and other applications, it is desired to monitor the time-response of the individual's pupil as the eye is subjected to various lighting conditions. As an example, such a device would measure the pupil response of a dark-adjusted eye that is subject to a stimulating light pulse (i.e. photostimulus). For such an example, the pupil, initially large due to the dark-adjusted state, will typically decrease in size in response to an external light stimulation flash, and then increase in size upon returning to a dark-adjusted condition.

Briefly, conventional pupilometers typically include optical-electronic apparatus for generating a pupillary response-inducing light stimulus, and for measuring the diameter of the stimulated pupil over a period of time to establish the response (including parameters such as pupil constriction velocity, initial, minimum and final pupil diameter, time to minimum, and reflex amplitude) of a user/subject's pupils to the light stimulus. To this end, conventional pupilometers typically include one or more visible light emitting diodes to produce the response-inducing light stimulus (i.e., diodes to generate a visible flash of light directed along an optical path and at the subject's eye to cause contraction of the subject's pupil), and infrared diodes or other IR source and associated optics and electronics adapted to direct the IR source to and from the subject's eye for measuring the dynamic pupillary response to the light stimulus.

Prior methods and apparatus for measuring pupillary response generally utilize either a pupil imaging technique or a light scattering detection technique.

Imaging methods and apparatus rely on imaging the eye (or a portion thereof) on a detection device such as charged-coupled device (CCD), or other optical detector array. In these instances, the image of the eye, or a portion thereof, is typically detected on a two-dimensional detection device or a scanning one-dimensional device. The output of the imaging device is processed to determine the size of the pupil or other desired pupillary response data. Examples of such imaging apparatus and methods are disclosed in Carter, U.S. Pat. No. 5,187,506; Carter, U.S. Pat. No. 5,646,709; and Carter, U.S. Pat. No. 5,661,538, Portable Self-Measurement Pupillometer with Active Opto-Electronic Centering Aid and Method of use Thereof.

Among the known prior pupil-imaging pupillometer techniques, further distinction can be made by the imaging illumination or detection method. Techniques for both iris illumination (see e.g., Gardner et al., U.S. Pat. No. 4,850,691, Method and Apparatus for Determining Pupillary Response Parameters) and retinal scatter are utilized. For the former, the image of the pupil appears darker than the surrounding iris due to the higher reflectance from the iris for the monitoring illumination. For the latter technique, the pupil is illuminated and the image of the eye is similar to that commonly know as 'red eye' in the photography industry. In this instance, the image of the pupil appears brighter than the surrounding iris due to the high scattering off the retina for the monitoring illumination conditions. Unfortunately, both of these prior imaging techniques suffer from difficulties in providing for proper alignment between the subject's eye and the detection device during response measurement.

Scattering pupilometers rely on the light scattered from the subject's eye under illumination from the monitoring illumination source. This scattered light is detected by a photo-detector element which converts the detected optical power to an electrical signal. The electrical signal output from the detection circuit is representative of the optical power incident on the active area of the photo-detector.

For example, the apparatus disclosed in Gardner et al. utilised a scattering technique which illuminates both the iris and the pupil area of the eye with the monitoring illumination. In this case, the detected signal is proportional to the scattered light from the illumination area. The output signal from the detector consists of a signal portion resulting from the illumination detected scattering from the iris, and a signal portion resulting from the illumination detected scattering from the retina. With the apparatus of Gardner et al. the scattering of the illumination light from the iris is greater than that from the retina, the major component in the output signal thus resulting from the scattering from the iris. Therefore, as the pupil contracts under light-constricting illumination, the output signal from the detector increases since the pupil decreases and the illuminated portion of the iris increases. A difficulty with this approach, as well as with other prior scattering-type pupilometers, is that the technique measures only relative pupil response; prior method and apparatus do not exist for absolute measurement of the pupil diameter during pupillary response measuring techniques.

In addition to the above-mentioned deficiencies in the prior art, there is a lack of practical pupillary response detection devices that will provide for a cost-effective imaging pupillometer, and particularly one that is relatively simple and compact, and thus suitable for use in portable, hand-held pupilometers.

BRIEF SUMMARY OF THE INVENTION

The general aim of the present invention is to provide for new and improved methods and apparatus that are relatively simple in construction and operation for the detection of pupil size and pupillary response to a light stimulus.

Another objective of the invention is to provide such methods and associated apparatus of relatively compact construction.

Yet another objective of the invention is to provide such relatively simple methods and compact apparatus that are suitable for direct, absolute pupillary size measurements.

A detailed objective of the invention is to achieve the foregoing by providing pupillary size detection apparatus providing (i) a first electrical signal indicative of the relative size and/or response parameters of an individual's pupil, and (i) a second electrical signal indicative of individual-specific parameters of the individual being tested, and associating the two signals so as to result in indication of absolute pupil size and/or pupillary response parameters.

Another detailed objective is to achieve the foregoing without the need for separate or additional calibration tests to be conducted on each individual prior to actual pupillary response testing.

These and other objectives and advantages of the invention will become more apparent from the following detailed description when taken in conjunction with the accompanying drawings.

Briefly, in a preferred embodiment, an apparatus according to the invention includes an IR source and optical apparatus for directing an IR beam toward an individual's pupil, a measuring channel comprising optical and photo-optical detecting apparatus for directing and receiving a first portion of the IR illumination leaving the individual's pupil and for providing an electrical output signal indicative of the illumination power detected, and a calibration channel comprising second optical and photo-optical apparatus adapted to receive a second portion of the IR illumination leaving the individual's pupil and for providing an electrical output signal indicative of certain individual-specific pupillary parameters. The output signal from the measuring channel, providing information regarding relative pupillary size changes when the pupil is light-stimulated, is processed with the output signal from the calibration channel to provide absolute or actual pupillary size and response data.

Figure 1:
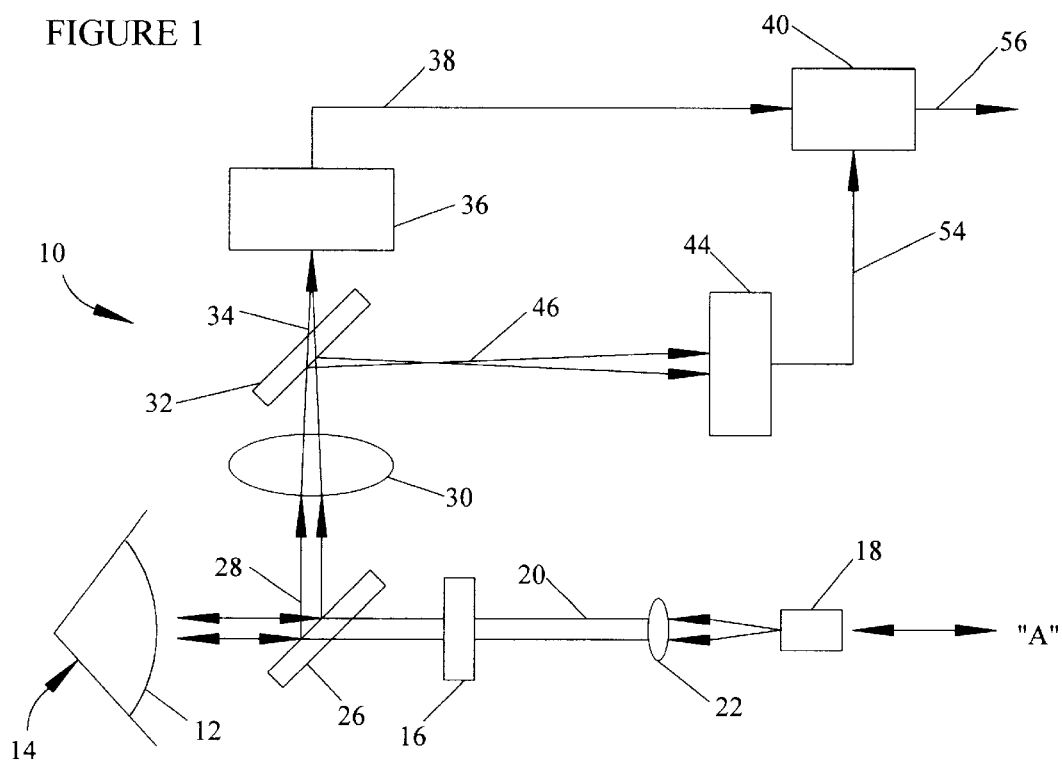
FIG. 1 is a diagrammatic view of one embodiment of apparatus suitable for detection of pupillary size and light-stimulated response data and incorporating the unique aspects of the present invention.

While the invention is susceptible of various modifications and alternative constructions, a certain illustrated embodiment has been shown in the drawings and will be described below in detail. It should be understood, however, that there is no intention to limit the invention to the specific form disclosed, but on the contrary, the intention is to cover all modifications, alternative constructions, and equivalents falling within the spirit and scope of the invention.

DETAILED DESCRIPTION OF THE INVENTION

For purposes of illustration, the present invention is shown in the drawings in connection with a pupillary size and response detecting and measuring apparatus 10 (FIG. 1) which is suitable for use in a pupilometer (not shown) such as of monocular, binocular, table-top, portable, or hand-held construction as known in the art for the detection and measurement of the response of an individual's pupil 12 to a light stimulus, and for operative association with test results or data display apparatus, data storage apparatus, data processing apparatus, and/or other apparatus adapted to receive the output from the detecting and measuring apparatus 10 such as may be typically associated with such pupilometers or as otherwise as desired.

To this end, the apparatus 10 includes one or more visible LEDs 16 suitably arranged, operatively connected to the pupilometer control mechanism, and operatively associated with appropriate optical components as required for the specific pupilometer embodiment such that flashing the visible LEDs results in a light stimulus directed toward the subject's eye 14 to which the test subject's pupil 12 responds. The positioning, operation and use of such visible LEDs and other light stimulus to generate a pupillary response is well known, with numerous alternate arrangements shown in the prior art. As will become apparent, the particular apparatus, arrangement and/or method for generating the pupillary response is not critical to the invention hereof, but can be selected/specified as convenient for the intended purpose or pupilometer design.

In accordance with one aspect of the present invention, the apparatus 10 is adapted to detect and measure both absolute, i.e. actual pupil size and pupillary response data, as well as relative pupillary size and response data. More specifically, the apparatus 10 determines the relative pupillary size, and response of an individual's pupil to LEDs 16 light stimulus, by detecting and measuring illumination exiting the individual's pupil, and then trimming or calibrating this relative data with certain individual-specific eye characteristics of the pupil being tested to generate actual pupillary size and response data. The invention also resides in the methods thereof and implementation into alternate embodiment apparatus. Advantageously, calibration of the relative size and response data for each individual or pupil being tested can be and is preferably accomplished at the same time, and with the same illumination (exiting the individual's pupil) that is utilized in detecting and measuring the individual's relative pupillary size and response data.

Figure 2:
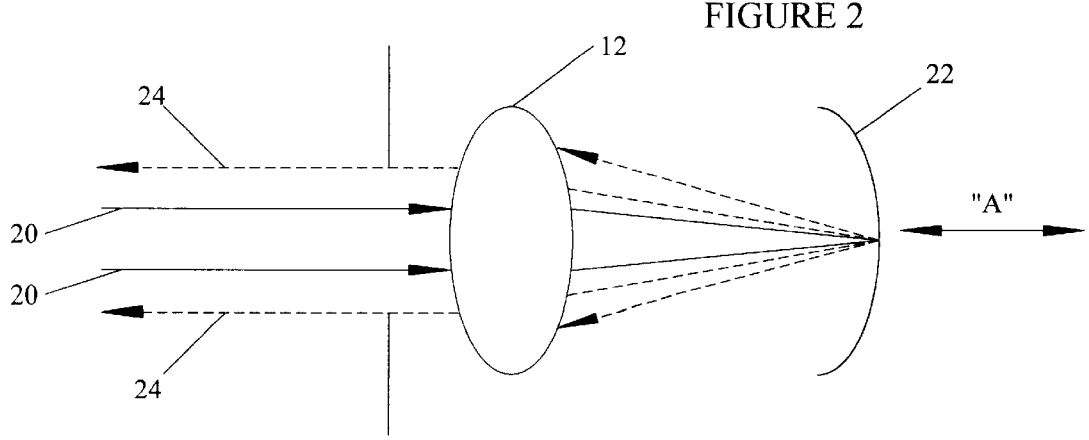
FIG. 2 is an enlarged diagrammatic view illustrating IR illumination entering and leaving an individual's pupil.

Initially, the test subject's pupil 12 is generally aligned along axis "A" with an infrared (IR) optical beam 20 (see FIG. 2) or IR source 18 (FIG. 1). The optical radiation passes through the individual's pupil 12, and to the back of the eye where it encounters the individual's retina 22 as the individual focuses on this beam. A small fraction of the light incident on the retina is scattered hemispherically. As illustrated in FIG. 2, some of the scattered light exists through the pupil in a substantially collimated optical output beam 24.

This light scattering effect can be clearly observed in flash photography with a phenomenon known as red-eye. Light exiting the flash bulb enters the pupil of the photographic subject, scatters from the retina, and a portion of the scattered light exists the pupil. The net effect is that the picture results in the subject's pupils appearing red since the scattered light is red in color due to the blood vessels in the retina. The present invention utilizes these light scattering properties and the illumination exiting the pupil to measure pupil diameter over a period of time to determine the pupillary response data to the pupilometer light stimulus.

Utilizing an apparatus capable of measuring optical power, collection of the scattered light exiting the test subject's pupil provides a relative measure of the pupil diameter and change in diameter. By way of example, suppose that two scattered light measurements are taken from the test subject within a few milli-seconds. If the pupil diameter remains constant during this time, the optical power output from the pupil will also remain constant. If the pupil decreases in diameter, the optical power will also decrease. If, for example, the pupil diameter decreases by a factor of 1.414 between the first and second measurement, the area of the pupil is reduced by a factor of 2 and the expected optical power output is also reduced by a factor of 2. By continuously monitoring the optical power exiting the pupil as a function of time, this technique provides continuous relative pupillary response measuring capability. As discussed further below, a "measurement channel" of apparatus 10 provides this relative pupillary response data. As also discussed further below, this measurement alone cannot provide the actual pupil diameter due to variations in the scattering properties from person-to-person, it can, however, provide a relative measurement of the change in pupil diameter.

In the present instance, an IR illumination source 18 such as an IR LED or laser creates a preferably collimated beam 20 of approximately 1 I mm diameter directed toward the individual's pupil 12 for the purpose of measuring relative pupillary response to the visible light stimulus 16. An IR input source is preferred because the retina does not respond to IR radiation. And as human pupils are typically 6–8 mm in diameter in low light levels, a beam size such as 1 mm is forgiving of some mis-alignment of the subject's eye on axis "A" while still allowing entry of the entire input beam into the subject's pupil.

When the optical input IR beam 20 passes through the subject's pupil 12 and encounter's the retina 22, some of the light is absorbed, as previously mentioned, and some of the light is scattered. This scattered light spreads approximately uniformly towards the front surface of the eye as indicated in FIG. 2. A portion of the scattered light exits the pupil while the remainder is absorbed in the eye. Assuming the subject's eye 14 is focused at infinity, the eye will automatically focus the input beam on the retina, and in this instance, the light leaving the eye is approximately collimated. Thus, collection and measurement of the optical power of the IR illumination exiting the subject's eye, for the purpose of determining relative pupillary response to the light stimulus 16, is straight forward using a photo-detector element and associated processing techniques.

However, from this single power measurement, it is not possible to measure the exact pupil diameter without calibrating the test data to the individual being tested. It can be shown that the optical power exiting the pupil can be estimated by the equation:

$$P_{out} = cP_{in}D^2/d^2$$

where $P_{out}$ is the optical power exiting the pupil (such as in beam 24), c is an unknown constant, $P_{in}$ is the input optical power (such as in beam 20), D is the pupil diameter, and d is the pupil to retina distance. Although the constant c is similar from person-to-person, it can in-fact be affected by several factors, and, of course, the dimension d will vary from person-to-person. As an example from actual test data, if $P_{in}$=40mW, $P_{out}$=25nW, D=7mm and d=19mm, then c=0.0046. Using standard radiometry, this result implies that approximately 6% of the light incident on the retina is scattered from its surface. Fortunately at these very low input light levels, sufficient optical power exists to make pupillary measurement with known photo-detector elements.

Unfortunately, although relative change in pupil diameter can be easily measured with a photo-detector, as apparent from the above equation, actual pupil diameter can not be determined because c and d will differ from personto-person. In other words, the problem with making only one measurement is that two variables exist: $c/d^2$ and $D^2$. On the other hand, if the value of $c/d^2$ is known or can be determined for each user, absolute or actual pupillary response data can be generated. Previously, the only practical method of determining the $c/d^2$ parameter was to utilize separate, relatively expensive, and extremely alignment sensitive, imaging apparatus designed to take actual pupillary measurements.

In carrying out the present invention, apparatus is provided to automatically calibrate the relative test data or output signal from a conventional photo-detector element to automatically account for differences in the individuals tested. More specifically, apparatus is provided for taking a second measurement from the illumination exiting the subject's pupil, processing this second measurement to generate an output signal that is indicative of or a function of the parameter $c/d^2$ for the individual being tested, and then processing this information with the relative response indicative signal from said photo-detector element to generate actual pupillary size data, which when taken over a period of time results in associated actual pupillary dynamic response data.

In carrying out this aspect of the invention, the parameter $c/d^2$ is determined by measuring a subset of the optical power returning from the individual's pupil in a region of known diameter. In other words, the above equation is optically "solved" for a known diameter D for the individual being tested to determine the $c/d^2$ parameter. This information is then used to "solve" the same equation for the actual pupil diameter D and associated response of the pupil to the light stimulus.

Figure 3:
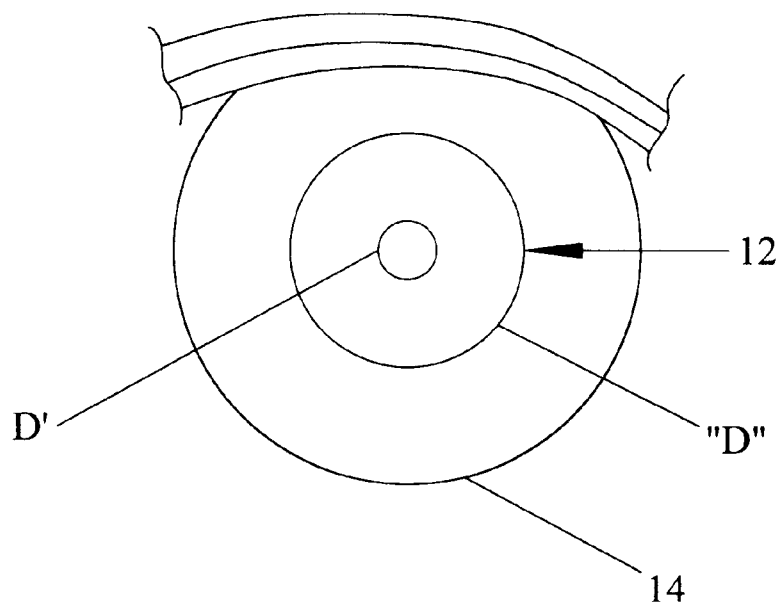
FIG. 3 is an enlarged diagrammatic view illustrating the two regions of an individual's pupil for which light is detected in accordance with the present invention.

This concept is generally illustrated in FIG. 3. The light exiting the pupil 12 through its diameter D is measured in a "measurement channel" including a photo-detector for detecting relative response data. By using a second optical system, discussed further below, the optical power for a known diameter D' region of the pupil is collected. Currently, it is envisioned that this subset diameter D' will be approximately 3 mm. This auxiliary measurement is made in a "calibration channel" which is then used to determine the unknown $c/d^2$ parameter for the individual being tested. Once these constants are determined, the optical power measured in the measurement channel can be directly converted to actual pupil diameter information. Measuring the optical power as a function of time directly yields the desired pupil diameter versus time information, and is particularly important when measuring the pupillary response to a light stimulus.

Referring to the preferred embodiment shown in FIG. 1, light emitting from IR source LED 18 is preferably collimated by lens 22, preferably a positive collimation lens. As previously mentioned, the input optical beam 20 is preferably limited in extent to approximately 1 mm diameter for entrance into the pupil 12. This optical beam passes through a 50%—50% beam splitter 26; half of the optical power is unused and half is directed along axis "A" for input into the subject's eye 14. Using techniques discussed below, the test subject aligns the pupil to be tested with the IR input beam 20. When aligned, an optical output beam 24 exists the eye with a diameter equal to that of the pupil diameter. Fifty percent of this return beam 24 is reflected to the measurement optics while the remainder passes through the beam splitter 26 and is unused. After reflection from the beam splitter 26, the optical beam 28 is focused by lens 30. A second 50%—50% beam splitter 32 directs one half of the focused light as beam 34 into the measurement channel photodetector 36 placed in the measurement channel at the point where the optical beam 34 comes to best focus. The output electrical signal 38 from this measurement channel photo-detector is amplified and processed at 40 to obtain the relative pupillary size and response data.

Figure 4:
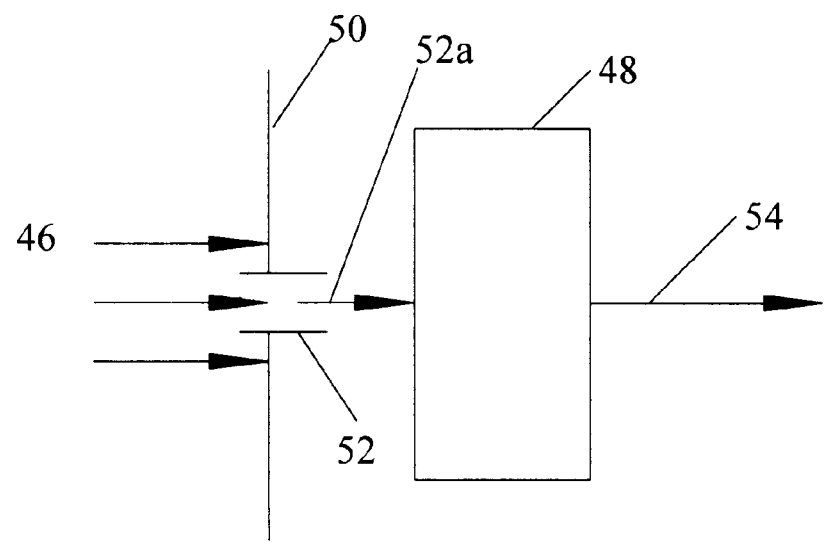
FIG. 4 is an enlarged diagrammatic view of certain parts of the apparatus of FIG. 1.

The calibration channel 44 is provided with a second photo-detector element 48 (FIG. 4) and means for determining the $c/d^2$ parameter for the individual being tested. In the embodiment shown, the second half 46 of the beam exiting beam splitter 32 is directed onto an apparatus plane 50 with a pinhole 52 of a known size so that a demagnified image of the pupil is formed at the pinhole. For example, in one embodiment, a 1.5 mm diameter pin hole is provided, and distances and lenses in the calibration channel are selected so that a 2X demagnification occurs between the pupil output and the plane of the pinhole. This results in light 52a from a 3 mm diameter region of the pupil passing through the pinhole. The second photo-detector 48 is positioned to detect the optical power in this portion of light resulting from the known 3 mm diameter portion of the pupil. As a result, the electrical output signal 54 from this second photo-detector element is indicative of the $c/d^2$ parameter for the individual being tested. In other words, this measurement provides the necessary calibration data to determine the unknown constants in the above equation, and utilizing known processing techniques with this calibration information, the output signal from the measurement channel can be scaled at 40 to obtain actual pupil diameter data, and provide signals 56 suitable for data storage, further data processing, and/or data display as desired.

It has been found that acceptable results are achieved if the photo-detectors and associated circuitry for both measurement and calibration channels are chosen to support pupil measurements at a rate of approximately 100 measurements per second. These rates could be substantially increased through known techniques, however, the benefits of increased measurement rates do not appear to justify the costs associated with such an increase with regard to uses in pupilometery.

It has also been found that, through optical design and selection of lenses, photodetectors, and the other optical and electrical elements, relatively large vision impairment, such as +/− 5 Diopters, is tolerable with no impact on the measurement ability of the apparatus 10. Thus if a test subject wears eyeglasses and must remove them to perform the test, no degradation is expected for even severe vision correction. Furthermore, users wearing contacts should experience no degradation since the contacts simply make the optical performance of the eye equivalent to a test subject without vision impairment.

During operation of the apparatus 10, it is desirable that the following conditions are simultaneously met: (1) all optical input power enters the pupil; (2) the eye focuses at infinity; and (3) the eye is positioned so that the light leaving the pupil can be collected by optical photodetectors.

Advantageously, all these objectives can be easily accomplished, even when testing an impaired or unwilling individual. While an IR beam is typically considered "invisible", it is possible to observe the presence of the beam from an IR LED or laser as both are weakly visible to the user as a red light. The alignment and focusing aspects of utilizing the apparatus 10 are then understood on the basis that the test subject can visually observe the approximately 1 mm diameter IR input beam 20. And the ease of meeting the alignment objectives, as further discussed below, is substantially enhanced when considered in connection with typical pupilometers that include some type of general forehead/eye positioning arrangement such as soft rubber cup(s) or bands for positioning around the subject's eye(s).

Utilizing a typical pupilometer, when the subject's pupil is in position to see the IR source 18, the natural reaction of the eye is to bring the optical beam 20 to a best focus on the retina. This forces the eye to focus at infinity and this satisfies the second requirement noted above.

The next aspect is to align the axis of the subject's eye with the input beam 20 along axis "A". Both the angle of the eye, relative to input optical beam angle, and the position of the pupil relative to the input beam must be set. If the test subject is offset in angle relative to the input beam, he or she will see the optical beam in the periphery of their vision. Fortunately when instructed to look at a light or an object, people tend to automatically adjust to center the object in their field of vision. Thus, simply instructing the willing user to focus on the visible IR beam automatically aligns the IR beam and eye axis angles to acceptable levels of precision.

The remaining alignment aspect is the pupil position. It has been found that a person can perceive when an optical beam is approximately centered in the pupil. This is accomplished in the following manner: (1) If the pupil is completely misaligned, no light is observed and the user starts searching for the optical beam. (2) If some of the optical beam is vingetted (i.e., partially blocked or truncated) by the edge of the pupil, a light reduction occurs and light scattering is obvious to the user. When instructed to move their eye until the light becomes brightest and most easily observed, the willing test subject can rapidly position the pupil to center the optical beam.

Preferably, the optical beam 20 enters approximately the center of the pupil, +/− approximately 1.5 mm. This insures that when the visible LEDs 16 are flashed to generate a pupillary response, the optical beam 20 will not be truncated by the shrinking pupil. Based on laboratory test data, willing test subjects are able to easily achieve these requirements, even when somewhat impaired.

To further assist the test subject in alignment, provision is made in the preferred embodiments to automatically check pupil alignment prior to initiating the visible light pulse from LEDs 16 that stimulate the eye. This automated process is accomplished by (1) monitoring the optical power collected from the pupil and insuring it meets a minimum criterion based on the power in the input beam 20, and (2) monitoring the optical power collected for stability over a period of time. This optical output is detected with the photo-detector element in the measurement channel 36, and made available to the test administrator as during the pupillary response testing. It has been found that it may take the test subject a few seconds to teach themselves how to align the pupilometer instrument with their eye, during which time large power fluctuations may be observed. However, once the test subject establishes proper alignment, it has been found that the optical power remains nearly constant until the light stimulus is applied.

Advantageously, monitoring of the optical power output by a test administrator prior to conducting the pupillary response test enables the administrator to determine when the pupil of even an unwilling subject is and is not properly aligned. Thus, the administrator can postpone the response testing until the subject becomes a "willing" subject, and has established sufficient alignment.

In view of the foregoing, it will be apparent to those skilled in the art that, although a preferred embodiment is shown in the drawings and discussed above, the apparatus and methods of the present invention include and be carried out in and with numerous alternate embodiments. While the apparatus 10 is shown in the drawings in connection with the testing of one pupil at a time, it will be apparent that apparatus according to the invention may also be adapted for dual-pupil testing, as well as simultaneous dual-pupil testing. It will be apparent to those skilled in the art that, although preferred, the input beam 20 need not be presented in a collimated state. It will be understood that the input beam 20 need not necessarily be IR illumination, i.e., from an IR source, but that other visible and non-visible wavelengths may be utilized in the methods and suitably designed optical circuits for injecting "light" into the subject's pupil and manipulation, detection and measurement of associated light exiting the pupil, including the use of many of the same photo-detector elements commercially available for use with IR wavelength illumination. It is noted that nothing herein limits the methods and apparatus of the present invention to a particular "look angle", i.e., orientation of the "A" axis in relation to the test subject or the test subject's head. Accordingly, it will be understood that the present invention is not limited to use and/or practice while the subject is looking or focusing "straight ahead" but is equally suitable for use with the subject looking an a arbitrary angle. It is also noted that nothing herein limits the methods and apparatus of the present invention to a particular relationship between the light directed into the subject's pupil and the light exiting the subject's pupil. Those skilled in the art will understand that, although the estimated relationship $P_{out} = cP_{in}D^2/d^2$ is presented and discussed above, nothing herein limits the present invention to use with this particular relationship, but that the methods and apparatus of the present invention are suitable and adaptable for use with other numeric or non-dimensional relationships (involving light entering and exiting the pupil, and/or including individual-specific eye characteristics related thereto) known or developed according theoretical or empirical techniques. It is further noted that, while desirable, nothing herein limits the methods and apparatus of the present invention to requiring that the eye be made to focus at locations to infinity. Accordingly, it will be understood that the present invention is not limited to use where the eye is required to focus to infinity. It will be further understood pursuant hereto that (except where such interpretation would be contrary to the understanding of the art) the terms "data" and "signal" are used generally interchangeably as is suitable in connection with the methods and/or apparatus under specific discussion, that a "signal" carries the "data" of interest or is representative of or indicative of such "data", and that the actual form of such data (such as the relative and actual pupil size and response data and calibration information) or signal thereof will take a form suitable for the particular embodiment and design specifics including but not limited to analog data/signals such as analog electrical signals, and digital data/signals such as electrical pulses, electromagnetic pulses or storage units, or other data/signal forms suitable for digital transmission and/or processing.

From the foregoing, it will also be apparent that the present invention brings to the art new and improved apparatus and methods for detecting pupillary size and response to a light stimulus. By virtue of providing unique optical calibration channel/apparatus adapted to provide a signal indicative of parameters of the specific individual being tested, the output signal from the measurement channel/apparatus can be processed for detecting and measuring both relative and absolute pupillary size and response data. And by providing the calibration signal from the IR illumination exiting the subject's pupil during the response testing, the absolute size and response data may be obtained without the need to perform additional testing on each individual prior or subsequent to the pupillary response test. By continuously monitoring the optical power exiting the pupil as a function of time, the apparatus 10 is uniquely adapted to provide continuous size data independent of whether or not relative pupillary size changes occur. As compared with prior optical measuring and detecting arrangements utilized in pupilometery, the apparatus 10 provides for a relatively low-cost, relatively simple arrangement, that is suitable for use as an enhanced replacement to such prior apparatus in pupilometers of all types, the apparatus 10 be capable of providing additional absolute data unavailable in such prior arrangement. Moreover, by virtue of its relatively compact design, the apparatus 10 is especially useful in portable hand-held pupilometers where size and weight are of substantial consideration. Clearly, these and other aspects of apparatus according to the invention provide for unique advancement in the art of obtaining pupillary size and light-stimulated response data.

I claim:

1. Apparatus for detecting pupillary response to a light stimulus comprising:

illumination source;

a first optical circuit directing an input beam from said illumination source into the individual's pupil along a first optical axis;

first means for providing a first signal indicative of the change in size of an individual's pupil in response to the light stimulus;

second means for providing a second signal indicative of individual-specific pupillary response parameters;

a second optical circuit directing a second illumination beam exiting from the individual's pupil toward said first and second signal providing means; and means operatively associating said first and second signals for generating an output signal indicative of the an individual's actual pupillary response to the light stimulus.

2. Apparatus as defined in claim 1 in which said second signal providing means is adapted to provide said response parameters independently of the response of the individual's pupil to the light stimulus.

3. Apparatus as defined in claim 1 further comprising an optical beam splitter positioned to direct one half of said second illumination beam toward each of said first and second signal providing means.

4. Apparatus as defined in claim 1 in which said second signal providing means senses only a fixed optical subset of said second beam exiting from the individual's pupil.

5. Apparatus for detecting the size of an individual's pupil comprising:

an IR illumination source;

first optical means for directing a first IR illumination beam from said IR source toward the individual's pupil;

second optical means for directing a second IR illumination beam exiting from the individual's pupil;

an optical beam splitter positioned and adapted to split said second beam into third and forth IR illumination beams;

first photo-optical detector means positioned to receive said third beam and adapted to provide a first electrical output signal indicative of the optical power contained in said third beam;

second photo-optical detection means positioned to receive said forth beam and adapted to provide a second electrical signal indicative of a subset of the optical power contained in said forth beam; and processing means receiving said first and second output signals and adapted to provide a third output signal indicative of the size of the individual's pupil.

6. Apparatus as defined in claim 5 in which said third output signal from said processing means in indicative of the actual pupillary size and response to the light stimulus.

7. Apparatus as defined in claim 5 in which said second photo-optical means includes an optical passage of a fixed diameter less than the diameter of said forth IR beam such that only a subset of said forth beam passes through said passage, and a photo-optical detector element operative to provide said second output signal at a level indicative of the optical power in said subset.

8. Method for detecting response of an individual's pupil to a light stimulus, said method comprising the steps of:

(A) illuminating the individual's pupil with a first light beam;

(B) processing an associated light beam exiting the individual's pupil to obtain a first signal indicative of the relative pupillary response to the light stimulus;

(C) further processing said associated light beam exiting the individual's pupil to obtain a second signal indicative of individual-specific parameters of the individual's eye; and (D) subsequently processing said first and second signals to obtain a third signal indicative of the actual pupillary response to the light stimulus.

9. A method as defined in claim 8 further comprising the step of (E) splitting said associated light beam exiting the individual's pupil into first and second beam portions each carrying response data in the form of optical power thereof; said processing and said further processing steps processing said first and second beam portions, respectively, for obtaining said first and second signals.

10. A method as defined in claim 8 in which said processing and said further processing steps occur simultaneously.

11. A method as defined in claim 8 in which said further processing step is adapted to obtain said individual-specific parameters independently of the individual's pupillary response to the light stimulus.

12. A method for detecting the size of an individual's pupil comprising the steps of:

(A) directing light into the pupil;

(B) detecting and measuring a first associated portion of the light exiting the pupil to obtain a first signal indicative of the entire associated light exiting the pupil;

(C) detecting and measuring a second associated portion of the light exiting the pupil to obtain a second signal indicative of a known subset of the associated light exiting the pupil; and (D) processing said first and second signals to obtain a third signal indicative of said size of the individual's pupil.

13. The method of claim 12 in which said first associated light portion is indicative of the entire associated light exiting the pupil.

14. The method of claim 13 in which said first associated light portion is a subset of the entire associated light exiting the pupil.

15. The method of claim 12 in which said second associated light portion is indicative of light exiting a first area of the pupil.

16. The method of claim 15 in which said second associated light portion is a subset of the light exiting said first area of the pupil.

17. The method of claim 12 in which said first and second signals are indicative of the optical power of said first and second associated light portions, respectively.

18. The method of claim 12 in which said first and second associated light portions are split from the associated light exiting the individual's pupil and from the entire associated light exiting the pupil.

19. A method for detecting the size of an individual's pupil comprising the steps of:

(A) directing light into the pupil;

(B) processing an associated portion of the light exiting the pupil to obtain a first signal indicative of the relative size of the pupil;

(C) further processing said associated light portion to obtain a second signal indicative of individual-specific eye characteristics relating the light entering the pupil and the associated light exiting the pupil; and (D) subsequently processing said first and second signals to obtain a third signal indicative of the actual size of the individual's pupil.

20. The method of claim 19 in which said associated light portion is indicative of the entire associated light exiting the pupil.

21. The method of claim 19 in which said associated light portion is a subset of the entire associated light exiting the pupil.

22. The method of claim 19 in which said processing step includes detecting and measuring a first portion of said associated light portion, and said further processing step includes detecting and measuring a second portion of said associated light portion.

23. The method of claim 22 further comprising the step of (E) providing first and second photo-detector elements for detecting and measuring said first and second portions, respectively, of said associated light portion.

24. The method of claim 23 in which said second photo-detector element detects light across a fixed area establishing said second portion of the associated light portion.

25. The method of claim 19 in which said processing and said further processing steps occur simultaneously.

26. A method for detecting response of an individual's pupil to a light stimulus comprising the steps of:

(A) directing light into the pupil;

(B) processing a first associated light portion exiting the pupil to obtain a first signal indicative of one of:

(i) the relative pupillary response to the light stimulus, and (ii) individual-specific eye characteristics relating the light entering the pupil and the associated light exiting the pupil;

(C) providing a second signal indicative of the other of:
   (i) said relative pupillary response, and
   (ii) said individual-specific eye characteristics; and (D) operatively associating said first and second signals to generate a third signal indicative of the actual pupillary response to the light stimulus.

27. The method of claim 26 in which said processing step includes the step of measuring a knowable subset of said first associated light portion to obtain said first signal indicative of said individual-specific eye characteristics.

28. The method of claim 26 in which said processing step includes processing said first associated light portion with an individual-independent characteristic to obtain said first signal indicative of said individual-specific eye characteristics.

29. A method for calibrating a first signal indicative of the relative size of individual's pupil, the method comprising the steps of:

(A) directing light into the individual's pupil;

(B) detecting an associated light portion exiting the individual's pupil;

(C) processing said associated light portion with an individual-independent characteristic into a second signal indicative of an individual-specific eye-characteristic; and (D) operatively associating said first and second signals to generate an output signal indicative of the individual's actual pupil size.

30. The method of claim 29 in which said associated light portion is a known subset of the entire associated light exiting the individual's pupil.

31. The method of claim 30 in which said associate light portion is associated with a known geometric characteristic smaller than the corresponding geometric characteristic for the individual's pupil.

32. The method of claim 31 in which said associated light portion is associated with a known diameter smaller that the diameter of the individual's pupil.

33. A method for detecting relative response of an individual's pupil to a light stimulus, the method of comprising the steps of;

(A) directing light into the individual's pupil;

(B) detecting an associated light portion exiting the pupil; and (C) processing said detected associated light portion into an output signal indicative of the individual's relative pupillary response to the light stimulus.

34. The method of claim 33 in which said processing step includes the steps of:

(i) measuring said associated light portion; and
(ii) generating an intermediate signal indicative of the light exiting the individual's pupil.

35. The method of claim 33 further comprising the steps of:

(D) providing a photo-detector element for detecting said associated light portion; and (E) directing said associated light portion to the photo-detector element.

36. A method for determining pupil size comprising the steps of;

(A) directing a beam of light into the pupil;

(B) detecting and measuring an associated portion of the light exiting the pupil; and (C) during said directing step, determining at least one of:
   (i) the size of the pupil, and
   (ii) the change in size of the pupil.

* * * * *